US010080835B2

(12) United States Patent
Lizari Illarramendi et al.

(10) Patent No.: US 10,080,835 B2
(45) Date of Patent: Sep. 25, 2018

(54) METHOD FOR THE AUTOMATIC FILLING OF CONTAINERS FOR MEDICATION FOR INTRAVENOUS ADMINISTRATION IN A MACHINE FOR THE AUTOMATIC PREPARATION OF INTRAVENOUS MEDICATION

(71) Applicant: KIRO GRIFOLS, S.L., Arrasate (ES)

(72) Inventors: Borja Lizari Illarramendi, Araico (ES); Naiara Telleria Garay, Arrasate-Mondragon (ES); Ainara Fol Ruiz de Loizaga, Vitoria-Gasteiz (ES)

(73) Assignee: Kiro Grifols, S.L., Arrasate (Gipuzkoa) (ES)

( * ) Notice: Subject to any disclaimer, the term of this patent is extended or adjusted under 35 U.S.C. 154(b) by 414 days.

(21) Appl. No.: 14/920,690

(22) Filed: Oct. 22, 2015

(65) Prior Publication Data

US 2016/0114097 A1 Apr. 28, 2016
US 2018/0071453 A9 Mar. 15, 2018

(30) Foreign Application Priority Data

Oct. 24, 2014 (ES) .................................. 201431570

(51) Int. Cl.
*B65B 1/04* (2006.01)
*A61M 5/14* (2006.01)
*B65B 3/00* (2006.01)

(52) U.S. Cl.
CPC .............. *A61M 5/14* (2013.01); *B65B 3/003* (2013.01); *A61M 2209/045* (2013.01)

(58) Field of Classification Search
CPC .. A61M 5/14; A61M 5/152; A61M 2209/045; A61M 5/148
See application file for complete search history.

(56) References Cited

U.S. PATENT DOCUMENTS

| 5,011,477 A * | 4/1991 | Winchell ............. A61M 5/1424 |
|---|---|---|
| | | 128/DIG. 12 |
| 2010/0241270 A1 | 9/2010 | Eliuk et al. |
| 2014/0311621 A1 | 10/2014 | Okuda et al. |

FOREIGN PATENT DOCUMENTS

| EP | 2742926 A1 | 6/2014 |
|---|---|---|
| WO | 95/15142 A1 | 6/1995 |
| WO | 2005/096776 A2 | 10/2005 |
| WO | 2012/172418 A2 | 12/2012 |

OTHER PUBLICATIONS

Search Report dated Oct. 20, 2015 in corresponding ES Application No. 201431570.

\* cited by examiner

*Primary Examiner* — Jason K Niesz
(74) *Attorney, Agent, or Firm* — Knobbe, Martens, Olson & Bear, LLP

(57) ABSTRACT

The invention describes a method for the automatic filling of containers for medication for intravenous administration in a machine for the automatic preparation of intravenous medication, the said containers comprising at least one fluid inlet connector closed by a cap that comprises an internal through conduit, said machine comprising injectors with spikes actuated by at least actuating means arranged in the said machine. The said method is characterized in that the said spike causes a piercing of one of the ends of said cap, allowing the direct injection of said component into said container.

11 Claims, 6 Drawing Sheets

METHOD FOR THE AUTOMATIC FILLING OF CONTAINERS FOR MEDICATION FOR INTRAVENOUS ADMINISTRATION IN A MACHINE FOR THE AUTOMATIC PREPARATION OF INTRAVENOUS MEDICATION

CROSS-REFERENCE TO RELATED APPLICATION

This application claims priority to Spanish Patent Application No. 201431570 filed on Oct. 24, 2014, the disclosure of which including the specification, the drawings, and the claims is hereby incorporated by reference in its entirety.

BACKGROUND OF THE INVENTION

The present invention is aimed at the sector of machines for the automatic preparation of intravenous medication used preferentially for cytostatic, cytotoxic and/or analgesic treatments, among others.

In particular, the present invention relates to a method used in machines of the said type for the automatic preparation of intravenous medication that comprises at least one robotic arm capable of preparing at least one mixture of medication for intravenous administration automatically and without manual intervention by the user.

SUMMARY OF THE INVENTION

Machines for the automatic preparation of intravenous medication are known in the state of the art, such as, for example, in the PCT patent application WO 2012/172418 or in the Spanish patent application 201430745. This type of machine allows, through the actuation of at least one actuator (which may be, for example, mechanical, electromechanical or robotic, among others), the preparation of a specific medication resulting from the mixture of different intravenous administration base components, such as, for example, a type of drug and a type of solvent, among others.

In the present invention, an intravenous administration component or a base component shall be considered to mean any medication, substance or drug for intravenous administration to patients, as well as any necessary solvent used for mixing with at least one medication, substance or drug for intravenous administration.

The base components used for obtaining the said mixtures are originally stored in special vials or bags, which are generally arranged in a specific area inside the machine. By means of a syringe supported and actuated by the actuator of the said machine, the volume of base component necessary for the desired medication mixture is drawn and deposited in a reservoir suitable for storing the mixture of the said base component with other base components previously deposited for the same medication mixture.

This type of reservoir in which the final mixture of medication for intravenous administration is stored is known as an "infusor" or "cassette". This type of reservoir, once filled with a medication mixture, can be used directly for the intravenous infusion of the said mixture in patients undergoing different treatments, mainly analgesic and/or cytostatic treatments, that involve long time periods of intravenous administration (between 24 and 72 hours) without the need for hospitalisation of the patients.

On the one hand, the "infusor" type of filling reservoir is a reservoir that comprises in its interior an inflatable elastomer bladder connected to an inlet port of the infusor, through which the different base components of the desired medication mixture are introduced. The base components of the mixture are introduced into the interior of the elastomer bladder, causing the said bladder to inflate. The said inlet port consists of a threaded female "Luer Lock" connector suitable for connection to any type of syringe or device having a male "Luer Lock" connector, allowing a hermetic and secure closure, preventing leaks and avoiding risks of direct contact. It should be noted that in the healthcare field, in a syringe whose distal extremity is of the type that comprises a "Luer Lock" connector, the said "Luer Lock" connector is referred to as male, while the point to which the said male "Luer Lock" connector connects is referred to as a female "Luer Lock" connector, such as, for example, the aforementioned inlet port of the infusor. In addition, the said infusor comprises an outlet port connected to a tube for direct intravenous administration to the patient and to allow intravenous infusion. The elastomer material of the infusor exerts a pressure on the liquid mixture contained in its interior, generating a more or less continuous outflow for a determined period of time. Finally, this type of infusor generally comprises a "Luer Lock" cap that allows the inlet port of the infusor to be aseptically closed and thus prevent the entry of bacteria or any undesired component and/or fluid into the interior of the reservoir.

On the other hand, the "cassette" type of reservoir is a reservoir that comprises in its interior a bladder connected to a single inlet/outlet point that connects to a tube for intravenous administration to the patient, whose distal extremity also comprises a female "Luer Lock" connector suitable for connection to any type of syringe or device with a male "Luer Lock" connector, allowing a hermetic and secure closure, preventing leaks and avoiding risks of direct contact. This type of reservoir, during the procedure of intravenous administration to the patient, connects via the administration tube with an electric pump that controls the speed of the outflow of the medication.

The methods known in the state of the art for filling reservoirs of the infusor or cassette types generally always require, before and after each filling, a prior manual step of connection and disconnection of the male "Luer Lock" connector of an injector (such as, for example, a syringe) to the female "Luer Lock" connector of a reservoir of the infusor or cassette type. This connection allows a hermetic screwed closure between the two "Luer Lock" connectors. Similarly, these two manual steps of connection and disconnection between the respective "Luer Lock" connectors of the injector and the reservoir respectively are repeated every time it is required to inject a component into a reservoir by means of an injector. In addition, once the corresponding component has been injected into the reservoir, it is also necessary to plug the female "Luer Lock" connector of the reservoir manually with a "Luer Lock" closure cap in order to aseptically close the inlet port of the reservoir and thus prevent the entry of bacteria or any undesired component and/or fluid into the interior of the reservoir. These manual steps of connection and disconnection of the "Luer Lock" connectors, which are carried out by healthcare staff authorised to perform this type of operation, considerably slow down the processes of filling and mixing of components in this type of reservoir and make it impossible to automate them, due to the need for a considerable technological sophistication that does not currently exist. In addition, in the manual filling of elastomer infusor reservoirs, the elastomer bladder exerts a pressure opposite to the force exerted by the healthcare staff during the process of filling this type of infusor. This resistance exerted by the elastomer bladder causes injuries to healthcare staff who regularly and very frequently carry out this procedure of filling elastomer infusors. Moreover, due to the high degree of toxicity of the drugs used for producing the requisite medications, the involvement of healthcare staff in phases or steps of the method for preparation of the said medications, such as, for example, the steps of connection and disconnection of the respective "Luer Lock" connectors between the injector and the reservoir respectively, or of manual filling of the infusors by means of syringes, can expose the said staff to a risk of contact with the said highly toxic drugs.

It is therefore desirable to find a solution that allows the cited drawbacks to be resolved. In particular, an aim of the present invention is to describe an efficient and automated method for filling intravenous administration reservoirs that makes it possible to accelerate the process of filling this type of reservoir by avoiding manual steps and reducing the risk of contact for healthcare staff in the preparation of these highly toxic products.

In order to solve the problems mentioned above, the present invention describes a method for the automatic filling of at least one type of base component in at least one container that comprises at least one fluid inlet connector, by means of at least injection means with spikes actuated by at least actuating means arranged in a machine for the automatic preparation of intravenous solutions, characterised in that the said spike causes a piercing of a closure cap of the container suitable for piercing and arranged in the said fluid inlet connector of the said container, allowing the direct injection of the said component into the interior of the said container. Thus, by having a pierceable cap, it is possible to directly pierce the said cap by means of an injection means, such as, for example, a syringe with a needle, and directly inject the base component into the interior of the reservoir, without the need for any connections and disconnections between the injection means and the reservoir. In addition, this approach avoids the participation of healthcare personnel and thus reduces any injuries that might be caused when carrying out manual procedures for the injection of components into the infusors. Furthermore, the present method makes it possible to reduce the risk for healthcare staff of contact with these highly toxic products.

Preferably, the fluid inlet connector and the closure cap are of the "Luer Lock" type.

Preferably, the said container is of the type used for direct intravenous infusion into patients.

In both the infusor and the cassette types of container, during the method for filling by means of machines for the automatic preparation of intravenous medication according to the present invention, in some cases there can be dosage losses of components for the final mixture that are not successfully introduced into the interior of the infusor or cassette and are deposited in the form of dead volumes in the interior of the said pierceable closure cap arranged in the fluid inlet connector of the container. Since control of the dosage introduced into a container of the infusor or cassette type is performed by means of a gravimetric weight check (i.e. using the density value of the base components to convert the calculated weight measurement into a volume value and thus determine the precise volume of the dosed base component), the calculated weight of the infusor or cassette that contains a dead volume of dose not administered to the patient causes an error in the calculation of the dose volume that has been administered to the patient. As is well known, in this type of treatment it is very important that the respective dose (by volume) of each base component intended to be used for the mixture should be exactly the dose that is finally deposited in the interior of the container of the infusor or cassette type, which is subsequently injected into the patient by infusion. Bearing in mind that the magnitude of the doses used in this type of mixture is frequently of the order of milliliters (ml), an error in the dosage of a base component for the mixture can produce irreversible consequences, including the death of the patient.

For all of the above reasons, preferably, after the direct injection of the said component into the interior of the said container, the spike recedes into the interior of the said cap and withdraws the dead volume of base component remaining in the interior of the said cap. This therefore provides an efficient and automated method for the filling of intravenous administration reservoirs that makes it possible to determine and know the exact dose volume of each base component introduced into the said reservoir.

Preferably, the said container comprises at least one inflatable elastomer bladder connected to the said fluid inlet connector and also comprises at least one outlet connected internally to the said inflatable bladder and connected externally to a tube for intravenous administration by infusion to the patient.

Preferably, the said container comprises at least one bag connected to a fluid inlet and outlet connector that is connected in its turn to a tube for intravenous administration by infusion into the patient.

Preferably, the injection means consist of a syringe with a plunger. In this case, after the direct injection of the said component into the interior of the said container, the syringe recedes into the interior of the said cap and withdraws the volume of the said base component remaining in the interior of the said cap, by means of the recession of the plunger of the said syringe.

Preferably, the injection means consist of a bag that contains a base component, the said bag being connected to a peristaltic pump that allows the said component to be pumped through a silicone tube connected to the said pump whose distal end is terminated with a spike. In addition, and in order to solve the problems mentioned previously, the present invention describes a method for the automatic filling of at least one type of base component, arranged originally in a first base container, into at least one second container for intravenous infusion that comprises at least one fluid inlet closed with a closure cap, by means of the action of at least several actuating means arranged in a machine for the automatic preparation of intravenous solutions, the said machine further comprising at least several injection means for transferring at least the said base component from the first container to the second container, the said method comprising the following steps:

(a) extraction of at least the said base component from the first container by means of the said injection means actuated by the said actuating means;
(b) weighing of the syringe with at least the said base component in its interior;
(c) piercing of the closure cap arranged in the fluid inlet of the second container by a needle of the said injection means;
(d) injection of the said base component into the said second container;
(e) extraction of the said needle from the said second container;
(f) weighing of the empty injection means.

The said method is characterised in that during the step of extraction of the needle from the said second container (step (e)), the actuator places the needle of the injection means in the interior of the cap, and by means of the withdrawal of the plunger of the said injection means, also actuated by the actuator, withdraws the volume of the said base component remaining in the interior of the said closure cap. In this way, by weighing the said injection means afterwards (step (f)), by means of the corresponding gravimetry calculation, it is possible to know the exact volume of dose deposited in the interior of the second reservoir, which will subsequently be used for intravenous administration by infusion to the patient.

Preferably, the base component may consist of a type of intravenous medication or a type of solvent.

Preferably, the first container may be a vial that contains at least one type of intravenous medication, or may be a bag that contains at least one type of solvent.

Preferably, the said second container for intravenous infusion comprises at least one inflatable elastomer bladder connected to a fluid inlet port and at least one outlet port connected to a tube for intravenous administration by infusion into the patient.

Preferably, the said second container for intravenous infusion comprises at least one bag connected to a fluid inlet and outlet port that is connected in its turn to a tube for intravenous administration by infusion to the patient.

Preferably, the actuating means arranged in a machine for the automatic preparation of intravenous solutions may consist of at least one actuator of the mechanical, electromechanical or robotic type, among others.

BRIEF DESCRIPTION OF THE DRAWINGS

For a clearer understanding of the invention, by way of explanatory but non-limitative example, some drawings are attached of a preferred implementation of the invention.

DETAILED DESCRIPTION OF THE PREFERRED EMBODIMENTS

Figure 1:
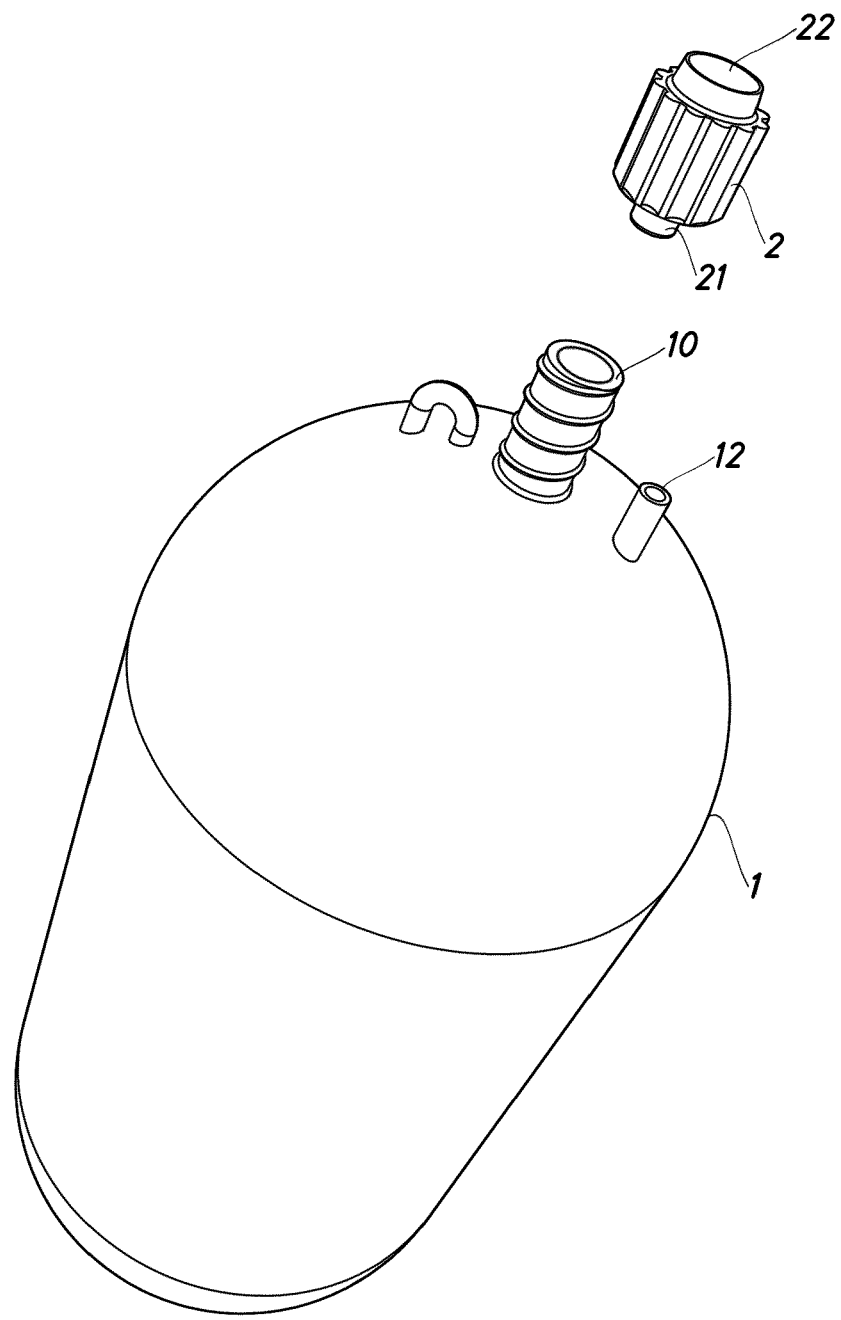
FIG. 1 shows a perspective view of a container or reservoir of the infusor type, together with a "Luer Lock" closure cap of the type used in the method according to the present invention.

FIG. 1 shows a type of reservoir -1- for the storage of a mixture of medication for intravenous administration according to the method of the present invention. Said type of reservoir illustrated in FIG. 1 is known as an "infusor" or an "elastomer infusor" and comprises, in its interior, an inflatable elastomer bladder -13- which, as can be seen in FIGS. 3 to 6, is connected to an inlet port -10- to the infusor -1- through which the different base components -7- for the desired medication mixture are introduced. Said inlet port -10- consists of a threaded female "Luer Lock" connector suitable for connection to any type of syringe or device having a male "Luer Lock" connector, allowing a hermetic and secure closure, preventing leaks and avoiding risks of direct contact. As has been mentioned previously, in the healthcare field, in a syringe whose distal end is of the type that comprises a "Luer Lock" connector, the said "Luer Lock" connector is referred to as male, while the point to which the said male "Luer Lock" connector connects is referred to as a female "Luer Lock" connector, such as, for example, the aforementioned inlet port -10- of the infusor -1-. In addition, the said infusor -1- comprises an outlet port -12-, connected to an intravenous administration tube (not illustrated) for connecting directly to the patient and thus allowing the intravenous infusion of the medication mixture. In this type of reservoir, the elastomer material exerts a pressure on the mixture liquid that it contains, generating a more or less continuous outflow to the patient for a determined period of time. As can also be seen in FIG. 1, this type of reservoir generally uses a closure cap -2-, of the "Luer Lock" type, which allows the inlet port -10- to the infusor -1- to be closed and thus prevent the entry of bacteria or any undesired component and/or fluid into the interior of the reservoir.

Figure 2:
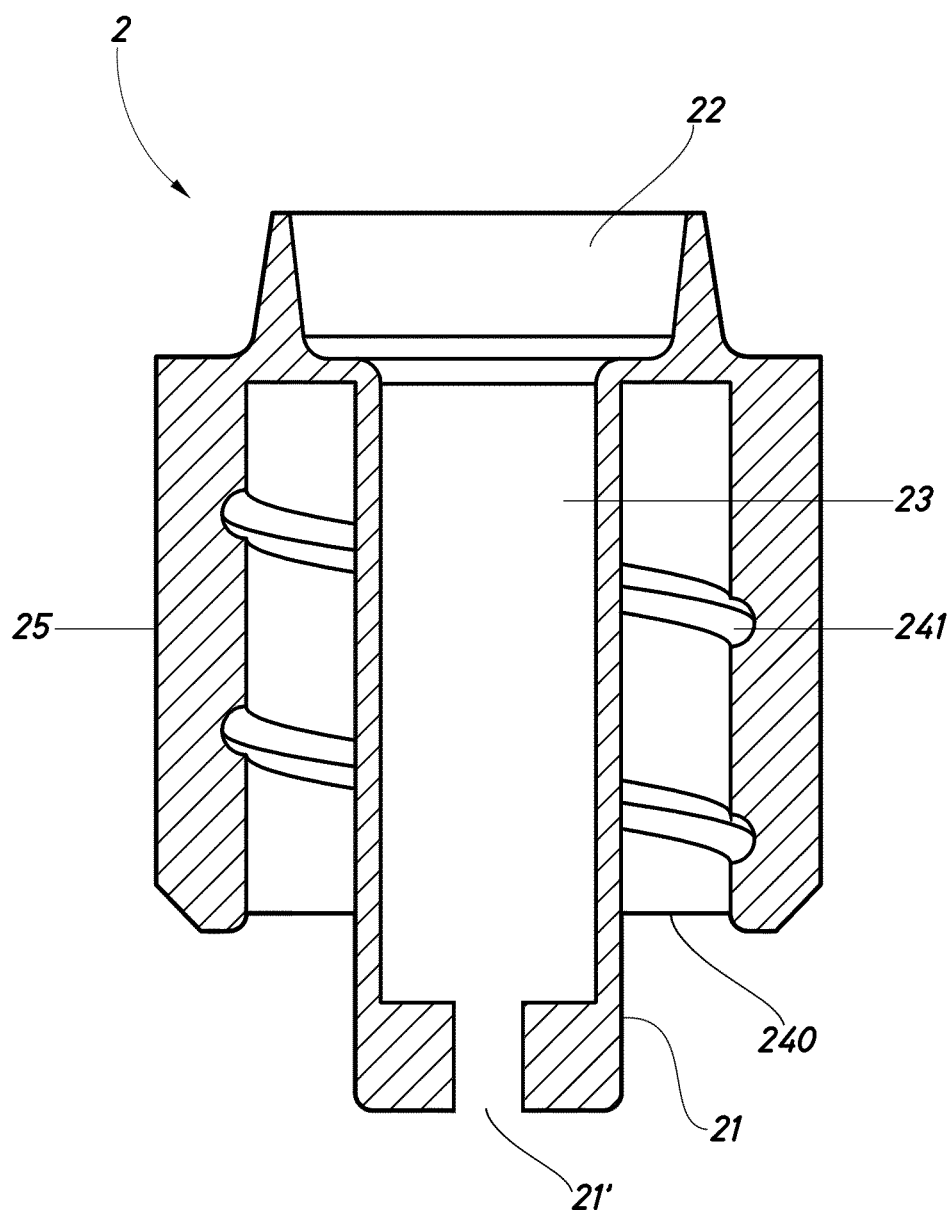
FIG. 2 shows a longitudinal cross-section of the "Luer Lock" cap of FIG. 1.

As can be seen in FIG. 2, said "Luer Lock" closure cap -2- consists of a cylindrical body -25- that comprises an internal volume -240-, open at one of its ends, whose internal surface comprises helical grooves -241- forming an internal thread for coupling with the "Luer Lock" inlet port -10- by means of the corresponding mating thread, as can be seen in FIGS. 3 to 6. In addition, said internal volume -240- comprises a cylindrical conduit -21- concentric with the said volume -240- that comprises an opening -21'- at one of its ends and the opposite end of the said conduit -21- coincides with the other end of the body -25- which comprises an orifice -22-. The interior -23- of said cylindrical conduit -21- passes through between the end -21'- and the end -22- for the possible passage of fluids. The said cylindrical conduit -21- has a diameter smaller than the diameter of the inlet port -10- of the infusor -1-, so that when the inlet port -10- is closed by means of the said closure cap -2-, the cylindrical conduit -21- penetrates the interior of the inlet port -10- at the same time that the inlet port is screwed into the interior of the internal volume -240-, creating an hermetic closure of the inlet port -10-. The orifice -22- may comprise a closure membrane capable of being pierced and penetrated by the needle -32- of the syringe -3-.

For the method described in the present invention, an intravenous medication container or reservoir of the infusor type may be used, or any other type of intravenous medication reservoir such as, for example, a reservoir of the cassette type (not illustrated). This type of reservoir generally comprises a bag in its interior connected to a single inlet/outlet port that connects to an intravenous administration tube for direct connection to the patient and whose distal extremity is also closed by means of a closure cap of the "Luer Lock" type as previously described, allowing closure of the inlet/outlet port of the cassette. During the procedure of intravenous administration to the patient, this type of reservoir is connected by means of the administration tube to an electronic pump that controls the speed of the outflow of the medication.

As has been previously explained, the present invention relates to a method used in a type of machine for the automatic preparation of intravenous medication, such as, for example, the machine described in the PCT patent application WO 2012/172418 or in the Spanish patent application 201430745. This type of machine allows, through the actuation of at least one actuator (such as, for example, a robotic arm), the preparation of a specific medication resulting from the mixture of different intravenous administration base components, such as, for example, a type of drug and a type of solvent, among others. In this type of machine, the general procedure for the automatic filling of reservoirs of the infusor or cassette type comprises steps that are not illustrated in the present description.

There follows a description of an example of the procedure of filling with a solvent by means of a peristaltic pump and of filling with a drug by using an actuator.

The procedure takes place according to the following steps, which are illustrated in FIGS. 3 to 6.

Step a): Manual Dosing of the Solvent by Means of a Peristaltic Pump (Not Illustrated)

In this first step, the filling of the infusor -1- with a solvent is carried out by means of a peristaltic pump connected by one end to a bag of base solvent and having on the other end a tube with a "Luer Lock" connector for connecting an infusor -1- or a vial by means of a disposable spike.

For the said filling procedure, a solvent dosing set is used. This comprises a silicone tube that connects with the bag of base solvent at one and, passes through the peristaltic pump and leaves one Luer Lock end free for the connection of the medication container (infusor -1-). Said silicone tube comprises a double channel in the central part, designed for connection to dual-channel peristaltic pumps, thus offering increased dosing accuracy. Also, in this case a spike has been added at one of the ends of the said silicone tube for piercing the bag of base solvent, and a "Luer Lock" connector at the other end for connecting the medication containers (infusor -1- with Luer Lock or disposable spike for the dosing of solvent in drug vials).

The said step a) comprises the following sub-steps carried out manually by the operator in interaction with the automatic medication preparation machine:

1. Purging of the peristaltic pump to eliminate any possible residues in the same;
2. Weighing of the empty infusor -1- on a scale attached to the machine;
3. Connection of the "Luer Lock" connector of the inlet port of the infusor -1- to the "Luer Lock" end of the dosing set connected to the peristaltic pump for the filling of the infusor -1- with physiological serum as solvent;
4. Disconnection of the infusor -1- from the dosing set at the "Luer Lock" end;
5. Placement of the "Luer Lock" cap -2- with membrane, also referred to as an addition point, by screwing the same by hand on to the inlet port to the infusor -1-;
6. Weighing of the infusor -1- on a scale attached to the machine and placement of a label for pre-identification of the final product;
7. Calculation by gravimetry of the dose volume of solvent introduced into the infusor -1-;
8. Placement of the infusor -1- in a container support of the machine by means of a holding clamp that holds the infusor -1- by the "Luer Lock" cap -2- or addition point;
9. Insertion of the clamp into the container support of the machine, carefully arranging the administration tubes of the infusor -1- in the upper part so as not to interfere with the movement of the actuator; the said infusor -1- is arranged in the container support of the machine in such a way that the "Luer Lock" cap -2- or addition point is arranged below the rest of the body of the infusor -1-;
10. Loading of the other materials necessary for the preparation of the medication (syringe -3- with needle, medication vials);
11. Closure of the window of the automatic medication preparation machine;

Step b) Automatic Dosing of the Drug into the Infusor -1-

Figure 3:
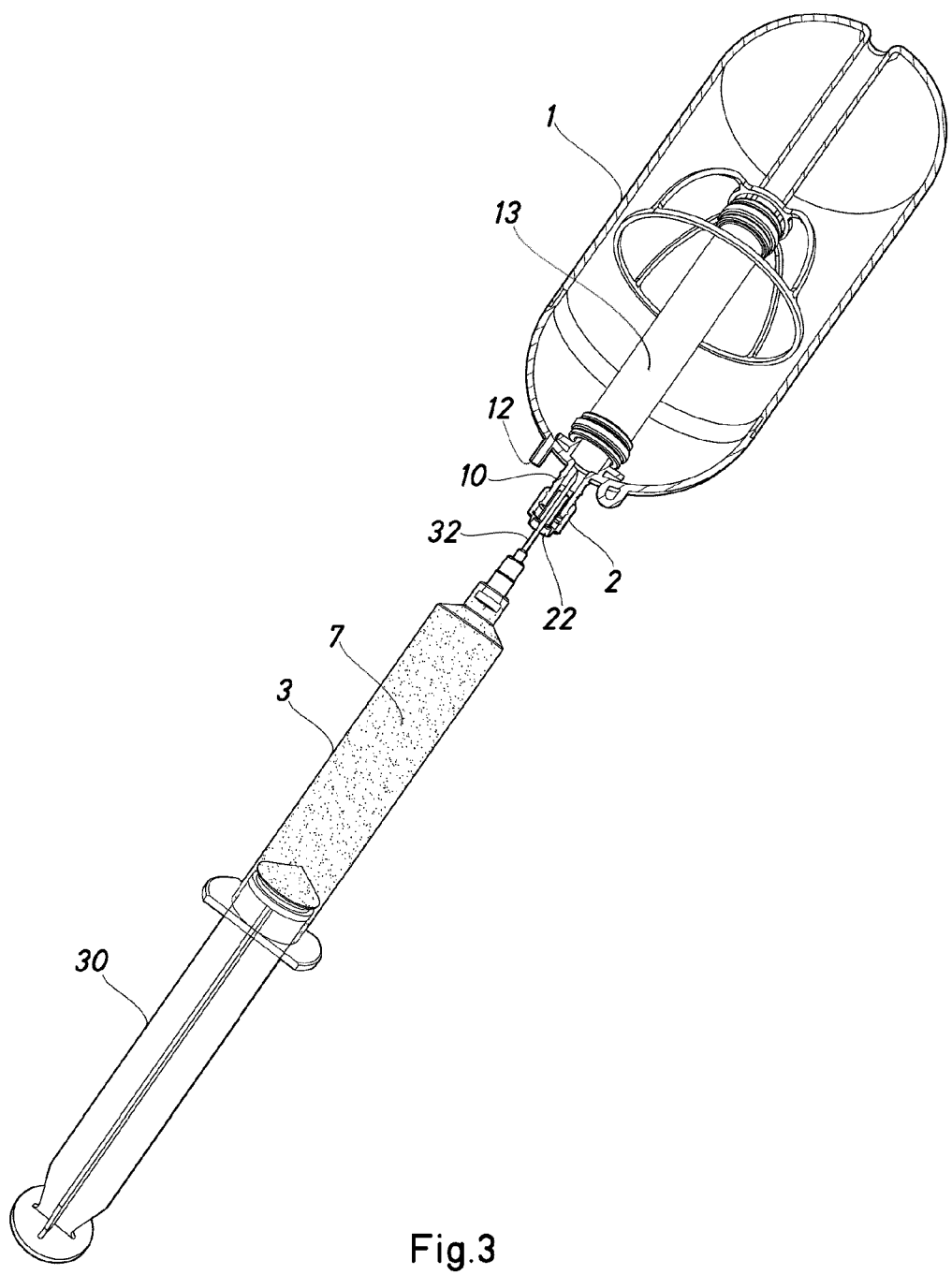
FIG. 3 shows a perspective view of a step of the method of the present invention in which the reservoir of the infusor type of FIG. 1 is filled by means of a syringe.
Figure 4:
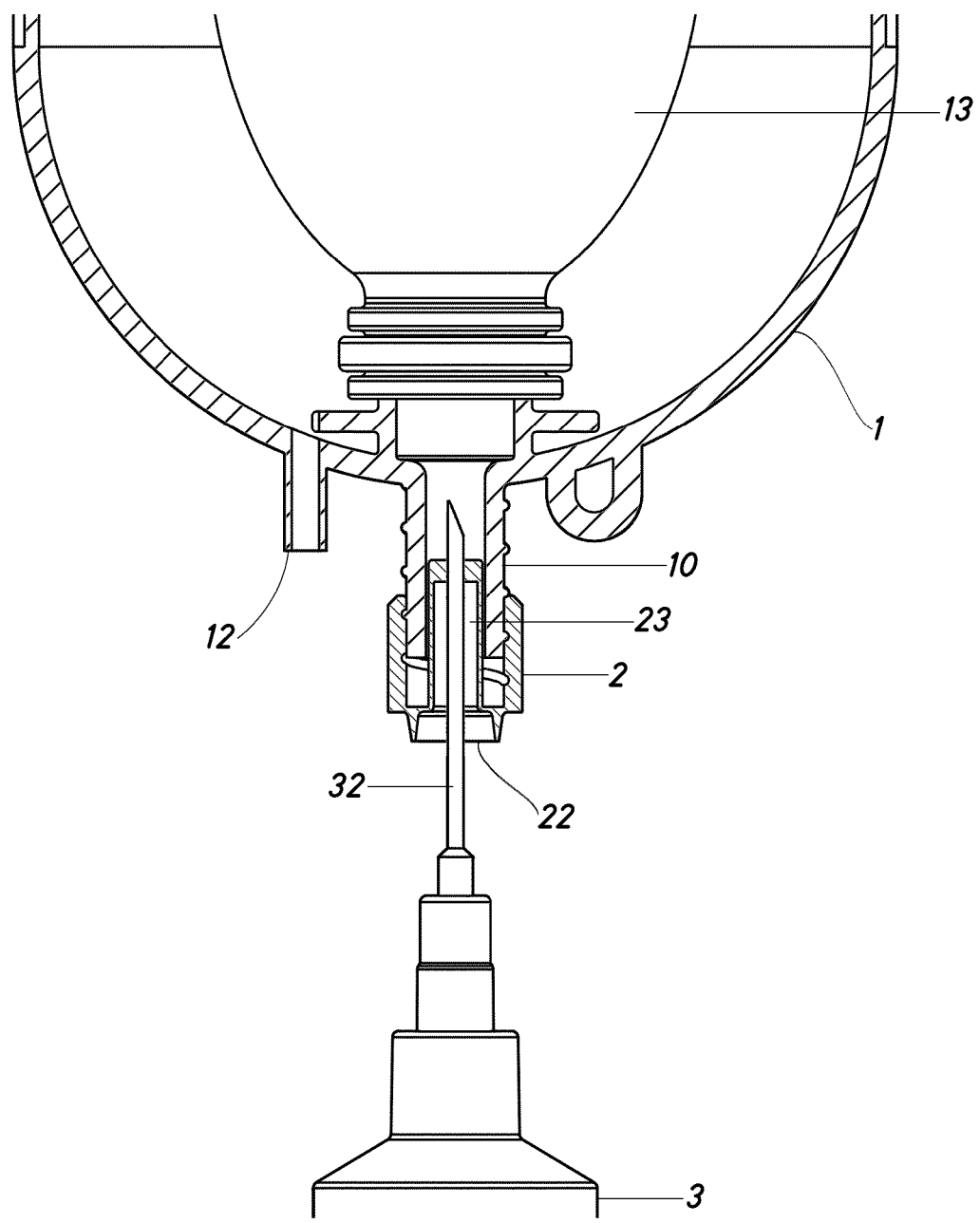
FIG. 4 shows an enlarged longitudinal cross-section view of a detail of FIG. 3, showing the insertion of the needle of the syringe into the interior of the "Luer Lock" closure cap connected to the infusor-type reservoir.
Figure 5:
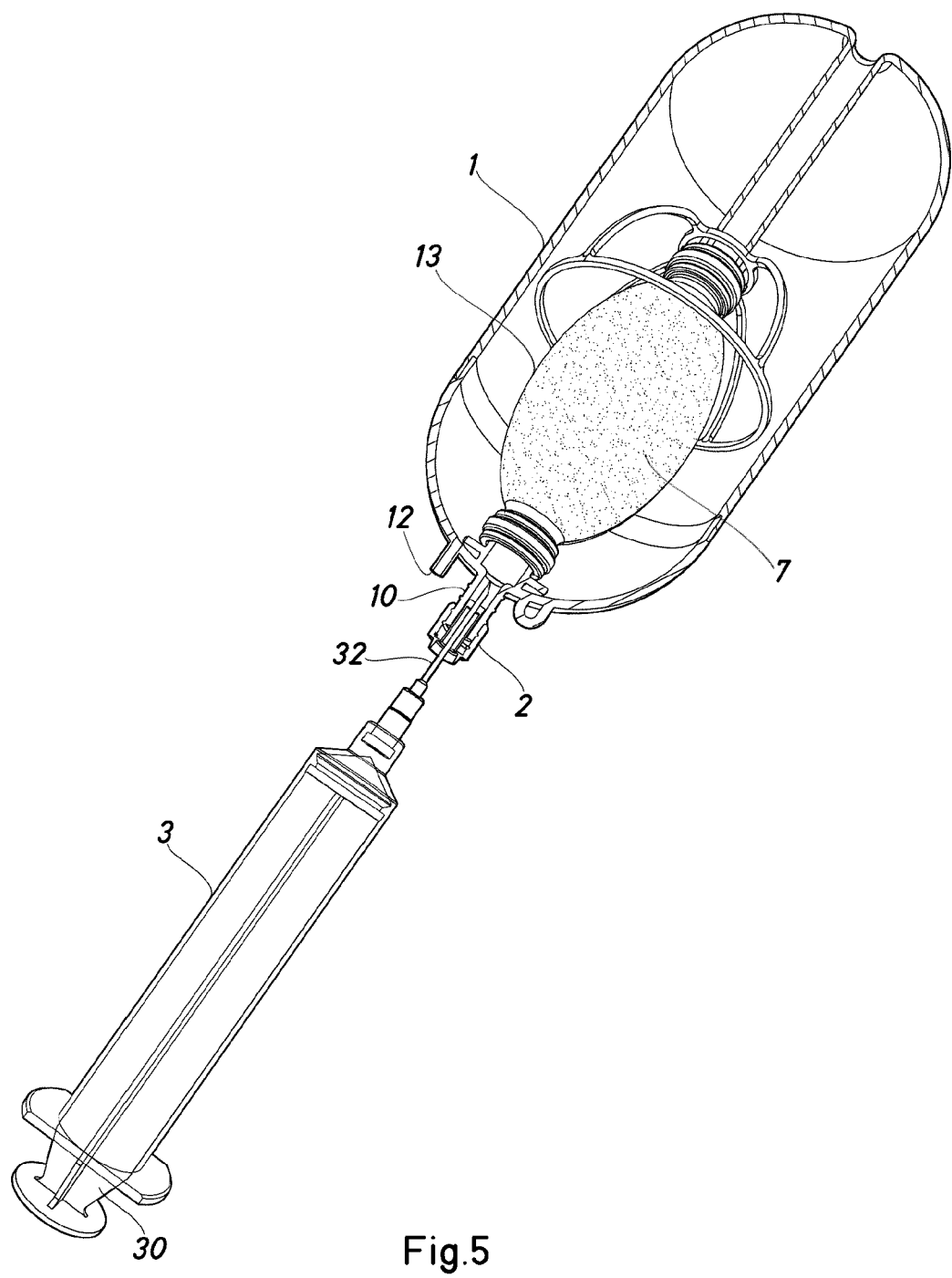
FIG. 5 shows a perspective view similar to that of FIG. 3 of a step of the method according to the present invention in which the contents of the syringe have been emptied into the infusor-type reservoir.
Figure 6:
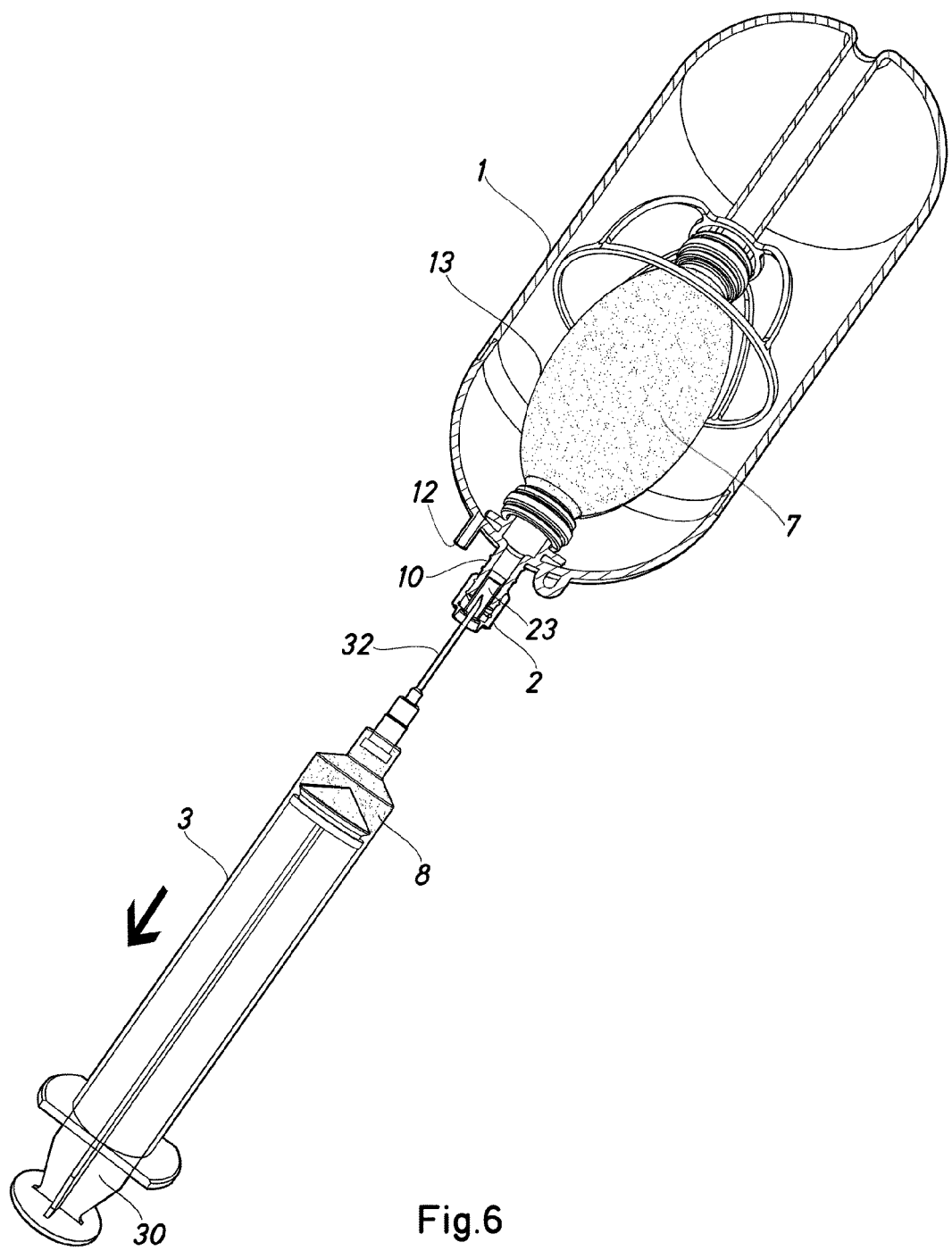
FIG. 6 shows perspective view similar to that of FIG. 5 of a step of the method according to according to the present invention in which the syringe is arranged to withdraw the dead volume of the dose from the closure cap of the reservoir.

12. Removal of the cover arranged over the needle -32-;
13. Optionally, a procedure can be carried out for detecting the absence of the cover by means of a module on the machine for detecting the absence of a cover;
14. Optionally, the syringe -3- can be weighed empty in order to calibrate the scale;
15. Automatic presentation of the vial with the desired drug for the mixture in the extraction position;
16. Extraction of the drug -7- from the vial by means of the actuation of the plunger -30- of the syringe -3- by an actuator that holds the body of the syringe -3- with a clamp;
17. Weighing of the full syringe -3- in order to check that the extracted dose of drug -7- is the correct one;
18. In this sub-step, as can be seen in FIG. 3, the needle -32-, by means of the actuation of the robotic arm that holds the syringe -3-, is positioned in such a way as to pierce the membrane arranged in the upper surface -22- of the "Luer Lock" cap -2- or additive addition, the latter being arranged in the inlet port -10- of the infusor -1-;
19. The dose of drug -7- is then injected directly into the infusor -1- by means of the actuation of the plunger -30- of the syringe -3- by the actuator that holds the body of the syringe -3- by means of a clamp. As can be seen in FIG. 5, as the drug -7- is introduced directly into the interior of the bladder -13- of the infusor -7-, the said bladder -13- is inflated to store the said drug -7- in its interior;
20. Once all of the drug -7- has been emptied into the interior of the infusor -1-, the needle -32- is extracted from the "Luer Lock" cap -2- or addition point. At this moment, as can be seen in FIG. 6, optionally the needle -32- is arranged, by means of the actuation of the actuator, in the interior -23- of the cylindrical conduit -21- of the said "Luer Lock" cap -2-, and, by means of a withdrawal of the plunger -30- of the syringe -3-, any possible volume -8- of drug dose remaining in the interior -23- of the cylindrical conduit -21- of the said "Luer Lock" -2- is extracted;
21. Optionally, in a final sub-step, the syringe -3- can be weighed and the dead volume of the syringe -3- calculated by means of gravimetry.

The said eventual volume -8-, referred to as "dead volume", is not introduced into the bladder -13- of the infusor -1- and will therefore not subsequently be administered to the patient. Notwithstanding, sub-step 20 makes it possible to know precisely the exact volume of dose introduced into the infusor -1- that will subsequently be used to administer directly to the patient the medication prepared in the said infusor -1-.

Sub-steps 12 to 21 (some of which are optional) can be repeated several times according to the number of different drugs necessary for the desired medication for the patient, without the need to make manual connections and disconnections between a syringe (without needle and with "Luer Lock" connector) and the inlet port -10- of the infusor -1-.

Finally, once the desired mixture has been created, a series of additional sub-steps may optionally be carried out:

22. The cover is placed on the needle -32-;
23. A detection process is carried out to check that the cover is in place, and the syringe -3- is withdrawn to a garbage bin arranged in the machine;
24. The motor preparation and initialisation data is automatically stored;
25. The infusor -1- is removed from the container support of the machine by extracting the holding clamp from the container support;
26. The pre-identification label of the infusor -1- is read in order to check that the correct product has been unloaded;
27. Weighing is carried out in order to check that the dose of drug introduced into the infusor -1- is the correct one;
28. Finally, an administration label is printed and glued to the infusor -1-.

Alternatively, the said method for the filling of the infusors -1- may be carried out both for filling with drugs extracted from vials and for solvents extracted from bags, such as, for example, physiological serum arranged in a base bag. Alternatively, therefore, the preamble of step a) and steps 2 to 4 could be removed and the filling with the solvent could be carried out automatically, as for the drug.

For automatic filling with solvent and drug, the following steps are followed:

B1. Preparation of the infusor -1- (as explained in points 5 and 6 above);
B2. Loading of the infusor -1- (as explained in points 8 to 11 above);
B3. Preparation of the syringe -3- (as explained in points 12 to 14 above);
B4. Extraction of solvent with the syringe -3- from an infusion bag located in another position in the same compartment that contains the infusor -1-;
B5. Weighing of the syringe -3- with solvent;
B6. Injection of the solvent into the infusor -1-;
B7. Automatic dosing of the drug (as explained in points 14 to 28 above).

Where a reservoir of the cassette type is used for filling with a mixture of drugs and solvent, completely automatic preparation may be advantageous even if it requires the occupation of a container position in the interior of the automatic preparation machine for positioning the bag of base solvent. The order of filling with the drug and the solvent may be programmed indiscriminately; some centres have a preference for filling with the solvent at the end, in order to leave the administration route of the cassette full of clean solvent.

The invention has been described by making reference to a preferred version of the same, purely by way of example. As will be understood, any expert in the subject, having the knowledge that follows from the present description, drawings and claims, will be able to introduce modifications to the object of the invention which, if they fall within the widest scope of the claims, will be understood to be covered by the scope of protection of the invention.

What is claimed is:

1. A method for the automatic filling of containers for medication for intravenous administration in a machine for the automatic preparation of intravenous medication, said containers being of the type that comprises at least one fluid inlet connector closed by a cap that comprises an internal through conduit, said machine being of the type that comprises at least injection means with a spike actuated by at least actuating means arranged in said machine, said method comprising:
   piercing one the ends of the said cap by said spike, and allowing a direct injection of said component into said container,
   wherein after the direct injection of said component into said container, the spike recedes into the interior of said conduit of said cap and withdraws the dead volume of base component remaining in the interior of the said conduit.
2. The method according to claim 1, wherein the base component consists of a type of intravenous medication.
3. The method according to claim 1, wherein the base component consists of a type of solvent.
4. The method for the automatic filling of at least one type of base component, according to claim 1, wherein said container is of the type used for direct intravenous infusion to patients.
5. The method according to claim 1, wherein said container comprises at least one inflatable elastomer bladder connected to said fluid inlet connector and also comprises at least one outlet port connected internally to said inflatable bladder and connected externally to a tube for intravenous administration by infusion to the patient.
6. The method according to claim 4, wherein said container comprises at least one bag connected to a fluid inlet and outlet port that is connected in its turn to a tube for intravenous administration by infusion to the patient.
7. The method according to claim 1, wherein said injection means consist of a syringe with a plunger.
8. The method according to claim 7, wherein after the direct injection of said component into the interior of said container, the syringe recedes into the interior of the said cap and withdraws a volume of the said base component remaining in the interior of the said cap, by means of the recession of the plunger of the said syringe.
9. The method according to claim 1, wherein the injection means consist of a bag that contains the base component, said bag being connected to a peristaltic pump that allows said component to be pumped through a silicone tube connected to said pump whose distal end is terminated with the spike.
10. The method according to claim 1, wherein the fluid inlet and/or outlet connectors and the closure cap are of the "Luer Lock" type.
11. The method for the automatic filling of containers for medication for intravenous administration in a machine for the automatic preparation of intravenous medication, said containers being of the type that comprises at least one fluid inlet connector closed by a cap that comprises an internal through conduit, said machine being of the type that comprises at least injection means with a spike actuated by at least actuating means arranged in said machine, said method comprising:
   piercing one of the ends of the said cap by said spike, and allowing a direct injection of said component into said container,
   wherein said injection means consist of a syringe with a plunger, and
   after the direct injection of said component into the interior of said container, the syringe recedes into the interior of the said cap and withdraws a volume of the said base component remaining in the interior of the said cap, by means of the recession of the plunger of the said syringe.

* * * * *

UNITED STATES PATENT AND TRADEMARK OFFICE
CERTIFICATE OF CORRECTION

PATENT NO. : 10,080,835 B2
APPLICATION NO. : 14/920690
DATED : September 25, 2018
INVENTOR(S) : Borja Lizari Illarramendi Page 1 of 1

It is certified that error appears in the above-identified patent and that said Letters Patent is hereby corrected as shown below:

On the Title Page

Item (30), in Foreign Application Priority Data, Line 2, change "201431570" to --P 201431570--.

In the Specification

Column 1, Line 12, change "201431570" to --P 201431570--.

In the Claims

In Column 10, Line 4, in Claim 1, change "one" to --one of--.

Signed and Sealed this
Twelfth Day of February, 2019

Andrei Iancu
*Director of the United States Patent and Trademark Office*